United States Patent
White et al.

(10) Patent No.: US 7,044,915 B2
(45) Date of Patent: *May 16, 2006

(54) SYSTEM AND METHOD FOR INTRALUMINAL IMAGING

(75) Inventors: David A. White, San Jose, CA (US); Alfred E. Williams, Fairfield, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/414,269

(22) Filed: Apr. 14, 2003

(65) Prior Publication Data

US 2004/0019279 A1    Jan. 29, 2004

Related U.S. Application Data

(63) Continuation of application No. 10/167,553, filed on Jun. 10, 2002, now Pat. No. 6,572,555, which is a continuation of application No. 10/041,894, filed on Jan. 7, 2002, now Pat. No. 6,443,903, which is a continuation of application No. 09/523,689, filed on Mar. 13, 2000, now Pat. No. 6,364,841, which is a continuation of application No. 09/150,001, filed on Sep. 8, 1998, now Pat. No. 6,050,949.

(60) Provisional application No. 60/059,718, filed on Sep. 22, 1997.

(51) Int. Cl.
*A61B 8/14* (2006.01)

(52) U.S. Cl. ...................... 600/459; 600/466

(58) Field of Classification Search ............... 600/454, 600/458–472, 585; 128/898, 916; 604/93–96; 606/159, 169–171

See application file for complete search history.

(56) References Cited

U.S. PATENT DOCUMENTS

| | | | | |
|---|---|---|---|---|
| 4,732,163 A | * | 3/1988 | Bonello et al. | 600/585 |
| 4,966,163 A | * | 10/1990 | Kraus et al. | 600/585 |
| 5,499,632 A | * | 3/1996 | Hill et al. | 600/585 |
| 6,050,949 A | * | 4/2000 | White et al. | 600/466 |
| 6,364,841 B1 | * | 4/2002 | White et al. | 600/466 |
| 6,443,903 B1 | * | 9/2002 | White et al. | 600/466 |
| 6,572,555 B1 | * | 6/2003 | White et al. | 600/466 |

* cited by examiner

*Primary Examiner*—Ali Imam
(74) *Attorney, Agent, or Firm*—Townsend and Townsend and Crew LLP

(57) ABSTRACT

A vascular catheter system comprises a catheter body having a proximal and distal portion and a single common lumen therebetween. The catheter body includes a first connector secured to the distal end of the proximal portion and a second connector secured to the proximal end of the distal portion. The connectors can be selectively connected to each other to join the lumens of the proximal and distal portions together in a continuous, axially fixed relationship. Disposed within the lumens, when the proximal and distal portions are joined together, is a drive cable. The drive cable may be movably, rotatable about its own longitudinal axis and carries at its distal end, a work element, which is typically an ultrasonic imaging transducer or interventional device. The lumen carrying the cable will be sufficiently large along a proximal portion to permit preferential collapse of the cable should rotation of the distal end become impeded. The catheter body may be made of a polymer or plastic material, such as polyetheretherketone (PEEK), which provides adequate bonding stiffness and resistance to kinking from large hoop stresses.

19 Claims, 5 Drawing Sheets

SYSTEM AND METHOD FOR INTRALUMINAL IMAGING

CROSS-REFERENCE TO RELATED APPLICATIONS

This application is a continuation of and claims the benefit of priority from U.S. patent application Ser. No. 10/167,553 filed Jun. 10, 2002, now U.S. Pat. No. 6,572,555 which is a continuation of U.S. patent application Ser. No. 10/041,894 filed Jan. 07, 2002, now U.S. Pat. No. 6,443,903 which is a continuation of U.S. patent application Ser. No. 09/523,689 filed Mar. 13, 2000, now U.S. Pat. No. 6,364,841 which is a continuation of U.S. patent application Ser. No. 09/150,001 filed Sep. 8, 1998, now U.S. Pat. No. 6,050,949 which claims benefit of U.S Provisional Patent Application No. 60/059,718 filed Sep. 22, 1997, the full disclosures of which are incorporated by reference.

BACKGROUND OF THE INVENTION

1. Field of the Invention

The present invention relates generally to medical devices and method and more particularly to a catheter system having a work element coupled to a drive cable disposed within a lumen of a flexible tubular catheter body.

2. Description of the Background Art

Arteriosclerosis, also known as atherosclerosis, is a common human ailment arising from the deposition of fatty-like substances, referred to as atheromas or plaque, on the walls of blood vessels. Such deposits occur in both the peripheral blood vessels, which feed the limbs of the body, and the coronary vessels, which feed the heart. When deposits accumulate in localized regions of a blood vessel, stenosis, or narrowing of the vascular channel, occurs. Blood flow is restricted and the person's health is at serious risk.

Numerous approaches for reducing and removing such vascular deposits are known, including balloon angioplasty, in which a balloon-tipped catheter is used to dilate a region of atheroma; atherectomy, in which a blade or cutting bit is used to sever and remove the atheroma; spark gap reduction, in which an electrical spark bums through the plaque; and laser angioplasty, in which laser energy is used to ablate at least a portion of the atheroma. In order to facilitate treatment of the stenosis, it is often desirable to obtain a visual image of the interior of the blood vessel within the region of interest. Catheters having imaging elements such as ultrasonic transducers are often used to obtain these images.

In many cases, catheter systems having imaging or interventional devices will include a rotatable drive cable disposed within the flexible catheter body. Catheters of this type will have some type of work element fixed to the distal end of the drive cable. In imaging systems, the work element is typically an ultrasonic transducer or a movable mirror associated with an ultrasonic transducer.

An exemplary catheter system having a rotating ultrasonic transducer coupled to a drive cable is disclosed in U.S. Pat. No. 4,794,931, the disclosure of which is incorporated herein by reference. In this system, a drive cable disposed within a flexible tubular catheter body is used to rotate an ultrasonic transducer about an axis parallel to the catheter body. The ultrasonic transducer is thereby caused to scan a region of the blood vessel in a plane normal to the catheter body.

Another catheter system, which may include an imaging or interventional work element connected to a rotating drive cable, is disclosed in U.S. Pat. No. 5,314,408, the disclosure of which is incorporated herein by reference. This "common lumen" catheter system includes a proximal region having multiple lumens for carrying a guidewire and various work elements and a reduced profile single lumen distal region. The catheter body may be formed from a single tubular member, which extends the entire distance from the proximal end to the distal end, or it may be formed from two or more tubular members which are joined together either in tandem or parallel. A catheter system of this type is advantageous in that the common lumen distal region, having a narrower profile, is able to enter into more constricted areas than would otherwise be possible.

A catheter of the type having a common distal lumen is used as follows. First, a guidewire is advanced into the patient until it lies within a region of interest, typically a region of stenosis within the blood vessel. After the guidewire is positioned, the proximal end of the guidewire is fed into the distal tip of the common lumen and the catheter is advanced into the patient over the guidewire. As the catheter advances into the patient, the guidewire enters and travels through a selected lumen of the multiple lumen proximal region of the catheter body.

Advancement of the catheter into the patient continues until the common lumen distal region lies within the blood vessel in the region of interest. The guidewire is then withdrawn into the proximal region to clear the common lumen. A suitable work element, often a rotating ultrasonic transducer, may then be advanced through the common lumen into the region of interest. Use of a catheter system of this type is described more fully in U.S. Pat. No. 5,314,408.

Marketing demands have created a need for a reduced outer diameter tubular catheter body. It is generally desirable to make the diameter of a catheter body as small as possible to allow the catheter to enter narrow and tortuous regions of the patient's vascular system. As the catheter body size is minimized, the strength of the catheter wall is decreased and the danger that the wall will rupture or collapse may become significant. A reduction in strength can lead to slight closure or collapse of the tubular structure under normal operating pressures incurred during a normal procedure. This type of failure causes an increase in friction on the drive cable, commonly referred to as NURD. The NURD effect can cause the motor powering the drive cable to be overworked causing a failure of the catheter.

To satisfy the market demand for smaller tubular catheter bodies, it would be desirable to replace the common lumen design with a single lumen design without sacrificing strength or pushability. To further meet the market requirements the outer diameter of the drive cable could be reduced, as well. An additional benefit of this reduction would be to improve catheter preparation, especially flushing, due to the increased clearance between the drive cable and the proximal tube design.

While the danger of catheter wall failure is present in any catheter system, it may be particularly troublesome in a common lumen catheter of the type described in U.S. Pat. No. 5,314,408. First, the common lumen is designed specifically to be small in diameter and to be positioned in particularly narrow and twisted regions of the vascular system. Second, the work element in a common lumen catheter not only rotates but also advances lengthwise through the lumen. When the rotating work element encounters a kink in the catheter body, it will impact the wall at the kink and in some cases may cause failure of the catheter body wall.

To avoid such failures, an attachment for a carrier, used to accommodate the work element, was designed that causes the carrier to track the lumen of the catheter body more reliably with less danger of puncturing the catheter wall. Such an improved tracking tip is disclosed in U.S. Pat. No. 5,458,585, the disclosure of which is incorporated herein by reference. While a significant improvement, use of the improved tracking tip can sometimes result in users confusing the solder ball, located at the distal end of the tracking tip, for the working element, when the procedure is viewed via x-ray. This leads to a mistaken determination by the user that the target location has been reached with the work element.

Another possible disadvantage of using the tracking tip is its effect on the shape of the work element carrier. The carrier is configured with the tracking tip coupled to its distal surface and the drive cable coupled to its proximal surface. The work element is by necessity, placed in a cavity between these two ends. As the housing travels through the catheter, bubbles may be created in the cavity. The trough configuration of the cavity causes the bubbles to be forced down upon the work element. The bubbles have a tendency to adhere to the surface of the work element. Since ultrasound does not travel through air bubbles, this phenomenon generally causes a blurred or smeared image to appear on viewing monitors.

The benefit of having a tracking tip in most catheter designs is, in essence, to ensure that a failure of the catheter wall will not occur when the work element housing is forced against it, as occurs when the tubular body is kinked or severely bent. Thus, a desired alternative to having a tracking tip would be realized by creating a system failure that occurs at a location other than the tube wall, such as, in the imaging core assembly. As an example, a reduced diameter drive cable can be incorporated into the tubular catheter body. Should the carrier encounter a kink or bend, the increased clearance between the tube inner diameter and the drive cable makes it possible for the drive cable to buckle or distort in a sinusoidal fashion within the tubular body. This buckling or distortion creates additional friction forces which quickly creates enough drag to cause the imaging core assembly to fail in a safe manner.

Commonly, catheter systems are designed to function as a single, integrated apparatus. Generally, the imaging core assembly, drive cable, and tubular catheter body are bonded together using thermal bonds or adhesives. Once formed the catheter is tested and certified for use in practice. If a catheter fails a performance test or fails in practice due to NURD or for other reasons, the entire device is discarded, regardless of where the failure occurs in the system. Moreover, a user having difficulties crossing a lesion, does not have the option to exchange the short guide wire engagement sheath (low stiffness) for the smaller profile longer guide wire engagement common lumen design (high stiffness). The user in this situation is forced to remove the catheter and begin the procedure again with a new catheter. Thus, creating waste and increased costs.

For these reasons, it would be desirable to provide an improved catheter system for use with internal work elements, such as ultrasonic imaging transducers. It would be particularly desirable to provide a catheter system that permits interchange or replacement of key components in the event that individual components fail or the catheter needs to be reconfigured. It would be further desirable if the drive cable of the catheter were configured to fail in a safe manner should the housing encounter a kink or severe bend which might restrict distal rotation of the cable. It would be still further desirable if the catheter body were formed from materials having improved physical properties, such as increased hoop strength and bonding stiffness. At least some of these objectives will be met by the invention described hereinafter.

SUMMARY OF THE INVENTION

According to the invention, a vascular catheter system is provided comprising a catheter body having a proximal portion and a distal portion both having a proximal end, a distal end and a primary lumen therebetween. This distal portion further includes a guidewire lumen preferably disposed coaxial with and distal to the primary lumen. A first connector is secured to the distal end of the proximal portion, and a second connector is secured to the proximal end of the distal portion. The connectors can be selectively connected to each other to join the primary lumens of the proximal and distal portions together in a continuous, axially fixed relationship. The guidewire lumen will usually be isolated or separated from the joined primary lumens. The first and second connectors may be, for example, mating Luer connectors. Disposed within the primary lumens, when the proximal and distal portions are joined together, is a drive cable. The drive cable is usually axially translatable within the joined lumens, is rotatable about its own longitudinal axis, and carries a work element at its distal end, typically being an ultrasonic imaging transducer but optionally being an interventional device.

In another aspect of the present invention, an improved catheter system includes (a) a tubular catheter body having a proximal portion, a distal portion, and a lumen therethrough, and (b) a drive cable rotatably received in the lumen. In a first aspect of the improved catheter system, the improvement comprises forming the flexible tubular body at least in part from a material capable of withstanding high hoop stresses. The material may be a polymer or plastic material, such as polyetheretherketone (PEEK), having increased hoop strength and bending stiffness.

In a second aspect, the improved catheter system of the present invention comprising preferably comprises a lumen having a proximal diameter which is enlarged relative to the distal diameter so that there is sufficient annular clearance in the proximal portion to localize drive cable failure to the proximal portion. Preferably, the enlarged lumen will be present over at least a proximal portion of the cable lumen to localize the failure of that portion of the catheter.

The present invention still further provides a method for positioning a work element within a selected region of a patient's vascular system. The catheter system used in the method comprises a catheter body having a proximal portion and a distal portion, both having a proximal end, a distal end and a lumen therebetween. The distal portion further comprises a guidewire lumen. The system also has a first connector secured to the distal end of the proximal portion and a second connector secured to the proximal end of the distal portion. The first and second connectors can be selectively connected to each other to join the lumens of the proximal and distal portions together in a continuous, axially fixed relationship. Moreover, a drive cable is provided disposed within the lumens when the proximal and distal portions are joined together.

The method utilizing this catheter system specifically includes advancing a guidewire into the patient's vascular system until it lies within the region of interest. A guidewire is then inserted into the guidewire lumen located at the distal end of the distal portion of the catheter body. The catheter body can be then advanced along the guidewire until the distal portion of the catheter lies within the region of interest. At this point, the work element, preferably an ultrasonic imaging transducer carried at the distal end of the drive cable, is in the proper position to perform its diagnostic or other function. After completing a procedure, the catheter body may be withdrawn from the patient's vascular system.

In an alternate preferred method a further step of exchanging the distal portion of the catheter body is provided. For example, a distal portion, having a short guidewire access lumen may not provide adequate stiffness for accessing a specific lesion in a patient's vascular system. Thus, the distal portion may be exchanged with a second distal portion, having a long guidewire access lumen which provides increased stiffness to the distal portion of the catheter body.

DESCRIPTION OF THE SPECIFIC EMBODIMENTS

Figure 1:
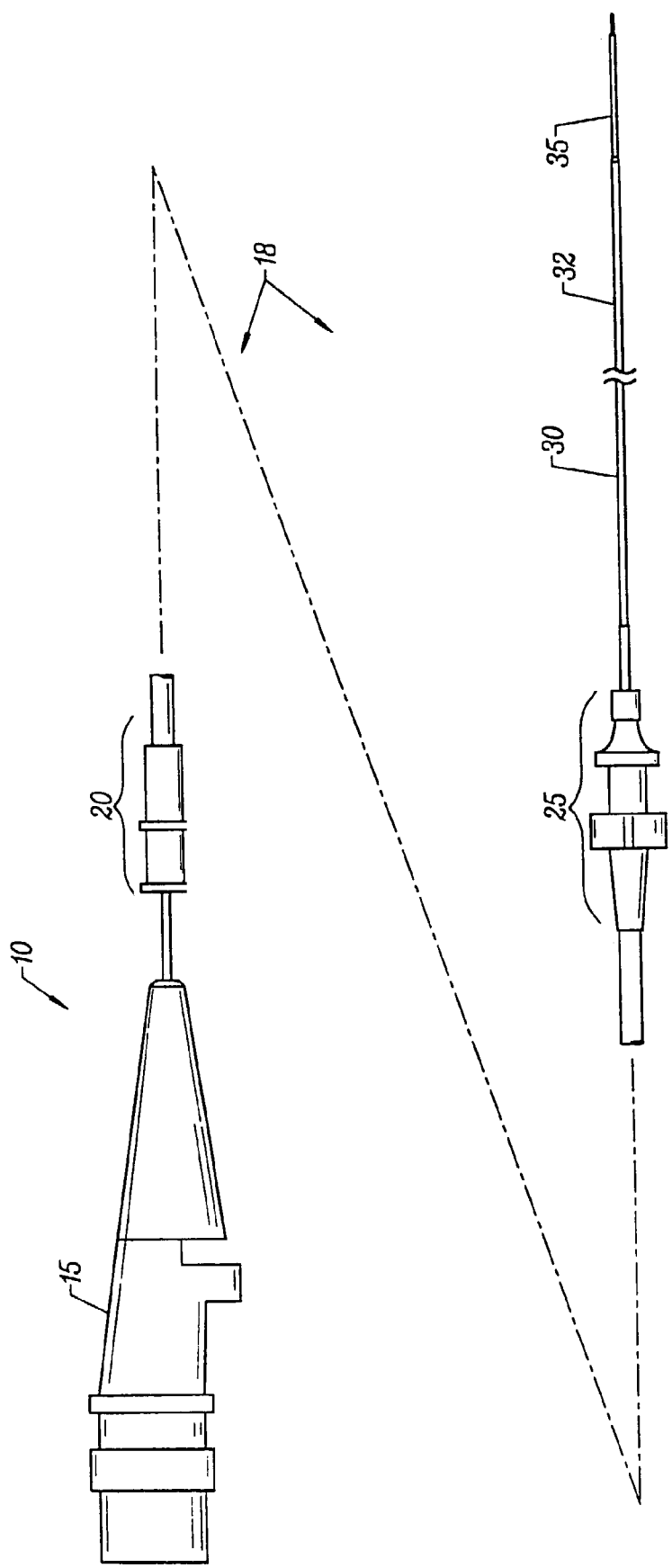
FIG. 1 illustrates an embodiment of a vascular catheter having a connector assembly according to the present invention.
Figure 2A:
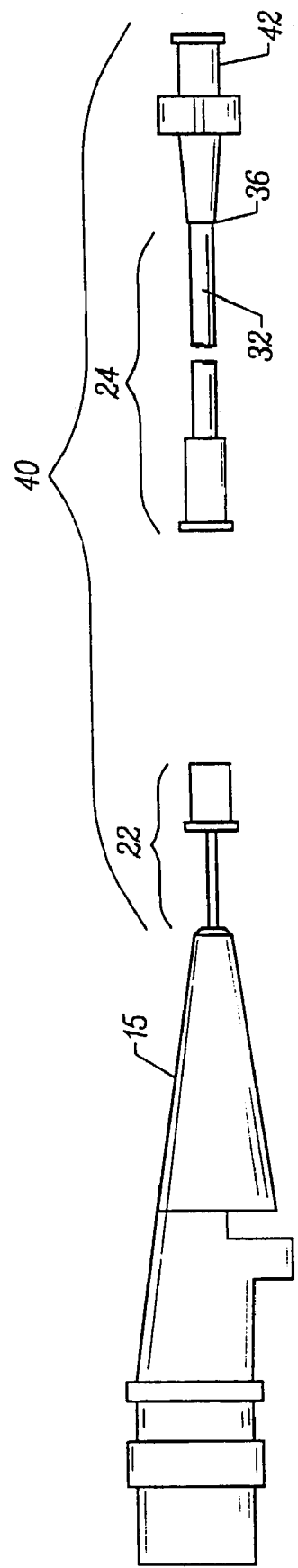
FIGS. 2A–2D illustrate the catheter of FIG. 1, having a hub, a proximal portion, further comprising a proximal tube and a distal tube, mating connectors, drive cable, and a distal portion of the catheter body.
Figure 2B:
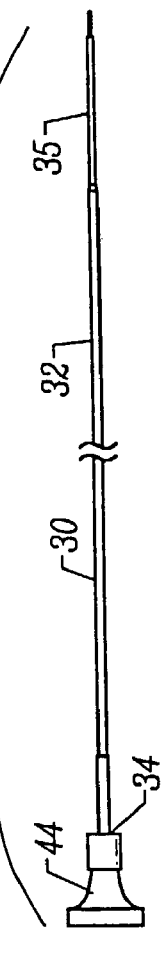
Figure 2C:
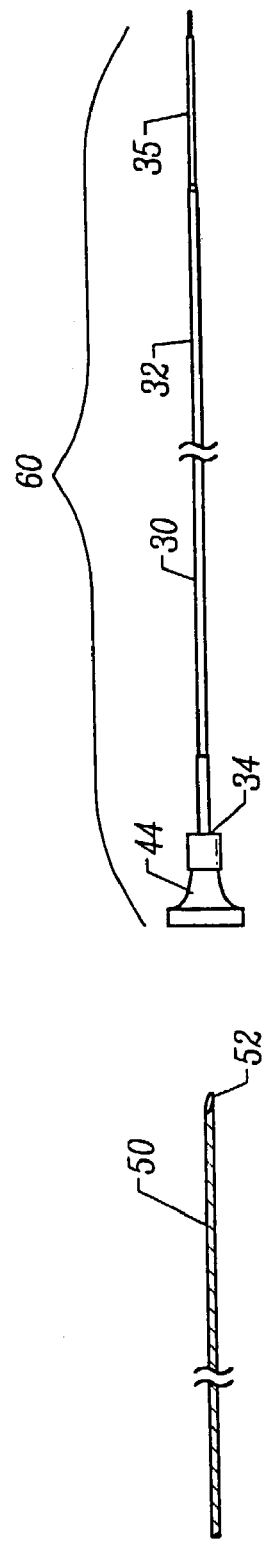
Figure 2D:

The present invention provides an improved vascular catheter system comprising a catheter body having a reduced profile distal portion to facilitate entry into coronary blood vessels and/or tight stenotic regions. The catheter body will comprise two regions, a proximal portion and a distal portion, each having a single common lumen therebetween. The distal portion will extend from the distal end of the catheter body to a point of adhesion to and including a connector. The proximal portion will extend from a point of adhesion to and including a second connector to the distal end of the tuning hub.

The proximal portion will have a somewhat larger cross-sectional area to accommodate a distal tube and a proximal tube, joined together in a telescopic engagement and used to increase the working length of the drive cable.

Preferably, the catheter body will be made of a polymer or plastic material, which increases the bending stiffness and has improved hoop strength, i.e. accommodates large hoop stresses. An exemplary material includes, for example, polyetheretherketone (PEEK).

The connectors joining the distal and proximal portions can be selectively connected to each other to join the lumens of the proximal and distal portions together in a continuous, axially fixed relationship. Mating female and male luer fittings are adhesively attached or molded to the proximal and distal portions of the catheter body, respectively.

Disposed within the lumens, when the proximal and distal portions are joined together, is a drive cable. The outer diameter of the drive cable may be varied to accommodate variations in size of the catheter body. The drive cable is movably, rotatable about its own longitudinal axis and carries at its distal end, a work element, which is typically an ultrasonic imaging transducer or other interventional device. A tuning hub is also provided and is located and secured to the proximal end of the drive cable.

At the distal end of the drive cable is the drive cable assembly comprising the drive cable and a carrier. The diameter of the drive cable is equal to or less than the size or diameter of the carrier. The carrier has a proximal end, a distal end, and a mounting surface which is open in the lateral and distal directions. Mounted within the mounting surface is an ultrasonic imaging transducer. The mounting surface defines an open substantially planar surface. It also has a second major surface intersecting the first surface at an angle of approximately 45 degrees.

A method is provided for positioning a work element within a selected region of a patient's vascular system. The catheter system used in the method is the system described above.

The method utilizing this catheter system specifically includes advancing a guidewire into the patient's vascular system until it lies within the region of interest. A proximal end of the guidewire is then inserted into a guidewire access lumen located at the distal end of the distal portion of the catheter body. The catheter body can be then advanced along the guidewire until the distal portion of the catheter lies within the region of interest. Usually, the catheter system will initially employ a distal portion having a short guidewire lumen. If the catheter system has difficulty in crossing the lesion, the catheter may be withdrawn and the distal portion exchanged for another distal portion having a longer lumen for engaging the guidewire.

After the catheter body is in position, the guidewire is retracted to evacuate the guidewire access lumen. The carrier disposed within the distal portion lumen is moved with respect to the catheter body to move the work element into the distal portion of the catheter body. At this point, the work element, preferably an ultrasonic imaging transducer carried at the distal end of the drive cable, is in the proper position to perform its diagnostic function. After completing a procedure, the catheter body is withdrawn from the patient's vascular system.

In an alternate preferred method the further step of exchanging or replacing the distal portion of the catheter body is provided.

Referring now to FIGS. 1 and 2, an improved vascular catheter system 10 is illustrated. The improved vascular catheter system 10 comprises a catheter body 18 having a reduced profile distal portion 60. The catheter body 18 will comprise a proximal portion 40 and a distal portion 60, each having a proximal end, a distal end, and a lumen 32 therebetween. The distal portion 60 will extend from the distal end of the catheter body 18 to an adhesive or other joint 34 to and including a female luer fitting 44. The proximal portion 40 will extend from the proximal hub 15 to a second adhesion or other joint 36 to and including the male luer fitting 42. The distal portion 60 will have a single lumen 32 extending through it and a reduced cross-sectional area to facilitate entry into coronary blood vessels and/or tight stenotic lesions. The proximal portion 40 will have a somewhat larger cross-sectional area to accommodate a distal tube 24 and a proximal tube 22 joined together in a telescopic engagement 20. By telescoping these two members with respect to one another, the operator may change the effective length of the catheter body. This will result in movement of the work element, axially translated by the drive cable 50.

Preferably, the catheter body 18 will be made of a polymer or plastic material, which provides adequate bending stiffness and resistance to substantially large hoop stresses. An exemplary material includes, for example, polyetheretherketone (PEEK). Catheter bodies having a high bending stiffness eliminates the need for stiffening mechanisms, such as a Nitinol™ stiffening mandrel. Moreover, the stiffer catheter body 18 can be made with a single lumen 32 as opposed to a dual lumen design. This configuration helps satisfy critical market demand for smaller diameter catheter bodies since the stiffer, single lumen catheter bodies can be made of a smaller diameter.

Figure 3:
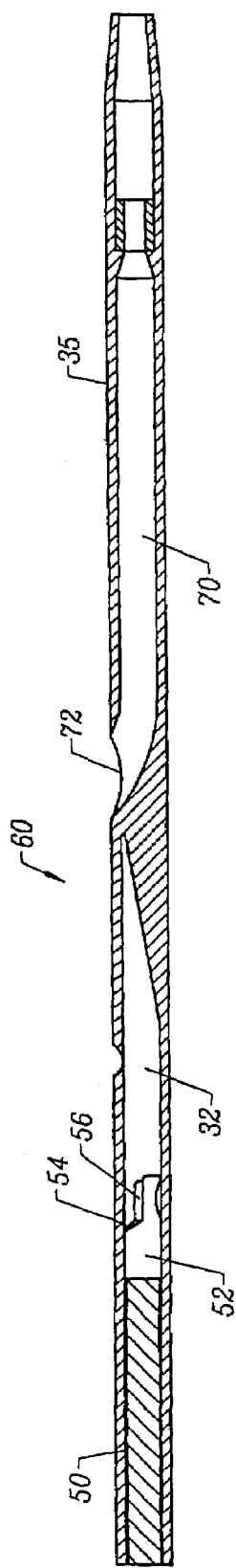
FIG. 3 illustrates the drive cable assembly disposed in the distal portion having a drive cable and a carrier, and also illustrating an access guidewire lumen.
Figure 3A:
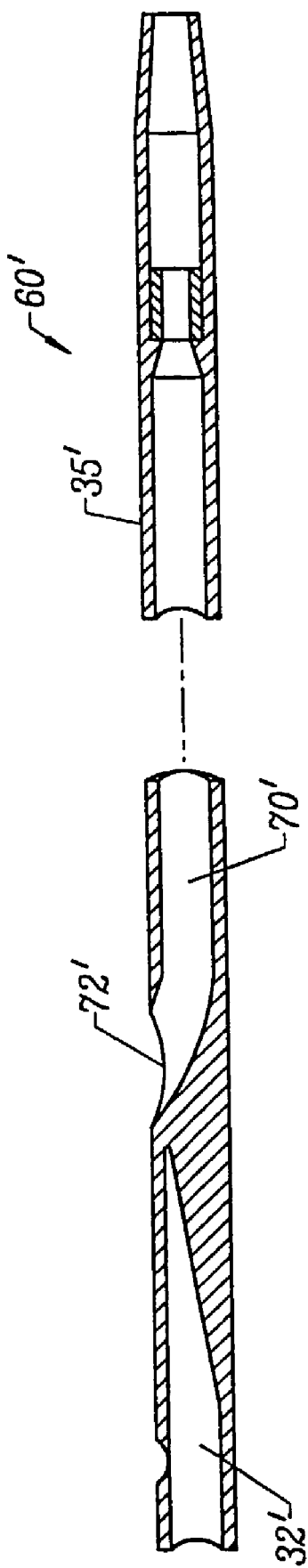
FIG. 3A is similar to FIG. 3, except that the distal portion is longer.

The mating connector assembly 25 includes a first connector or male luer fitting 42 secured to the distal end of the proximal portion 40 and a second connector or female luer fitting 44 secured to the proximal end of the distal portion 60. The mating connectors 25 joining the distal and proximal portions 60, 40 can be selectively connected to each other to join the lumens 32 of the proximal and distal portions 40, 60 together in a continuous, axially fixed relationship. Mating female and male luer fittings 44, 42 are adhesively attached or molded to the proximal and distal portions 40, 60 of the catheter body 18, respectively. In a preferred embodiment, the male luer fitting 42 will be adhesively attached 36 to the distal end of the telescope assembly 20. The female luer fitting 44 will be insert molded 34 to the proximal end of the proximal sheath 30. The use of the mating connector 25 will allow the user, who is having difficulty crossing a lesion, the option to exchange a distal sheath 35 with a short guidewire lumen 70, as shown in FIG. 3, for a sheath 35' having a longer distal portion 60', as shown in FIG. 3A. The user will also be allowed to replace failed parts attached to either the proximal or distal portions 40, 60 without having to discard the entire catheter system 10.

Disposed within the lumen 32, when the proximal and distal portions 40, 60 are joined together, is a drive cable 50. The outer diameter of the drive cable may be varied to accommodate variations in the size of the catheter body 18. For example, due to marketing demands, the outer diameter of the drive cable 50 is reduced from 0.029" to 0.022" so that the catheter body 18 could also be reduced in diameter. A benefit of such a reduction in size will be improved catheter preparation (specifically flushing), due to the increased clearance between the drive cable 50 and the catheter body 18. The drive cable 50 is movably rotatable about its own longitudinal axis and carries at its distal end a work element. The work element will often be an ultrasonic transducer 56 for imaging the interior of a blood vessel. Alternatively, the work element may be an interventional device such as a rotating cutter or laser ablation device for treating the blood vessel. The work element may even be in the form of an interventional device having an angioplasty balloon for reducing the stenosis by dilating a blood vessel.

Finally, a proximal hub 15 is also provided and is located and secured to the proximal end of the drive cable 50. The imaging catheters 10 are tuned or filtered electronically in the proximal hub 15. This is done to match the impedance of the entire electrical system (catheter, MDU, and system) in an attempt to optimize image artifacts. For example, when changes are made to the catheter design, the lead wires, or the catheter length, these changes would all potentially require tuning adjustments in the proximal hub 15.

FIG. 3 shows a more detailed view of the distal portion of the catheter body 60. At the proximal end of the distal portion of the catheter body 60 is disposed within the lumen 32 the drive cable assembly 55. A major advantage in the improved catheter system 10 having a connecting assembly 25 is that it can be reused if another region in the vascular anatomy needs treatment or diagnosis. To reuse the catheter system 10, the catheter is simply withdrawn from the patient and the guidewire is introduced into the new region. However, a major concern is the trackability of the catheter through varying tortuous anatomies. The distal portion 60 provides a guidewire access lumen 70 and a guidewire exit port 72 disposed within the distal sheath 35. The catheter system 10 can be reinserted over the repositioned guidewire as either a short lumen rapid exchange catheter or a long lumen rapid exchange catheter is used.

Figure 4:
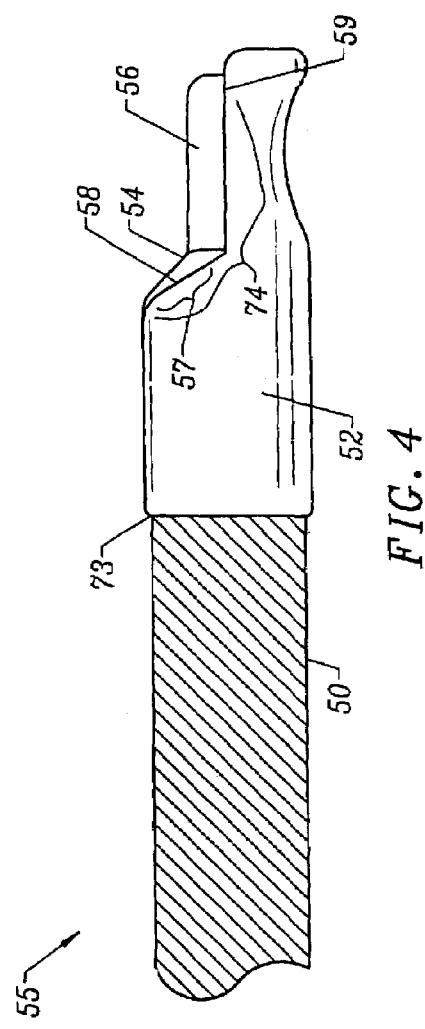
FIG. 4 illustrates the drive cable assembly having a drive cable, a carrier, and an ultrasonic imaging transducer.

Referring now to FIG. 4, an enlarged illustration of the drive cable assembly 55 is illustrated. The drive cable assembly 55 is coupled to the distal end of the drive cable 50. The drive cable assembly 55 is comprised of the drive cable 50 and a carrier 52. Preferably, the diameter of the drive cable 50 is less than the size or the diameter of the carrier 73. The benefit from having such a configuration will be described fully with regard to FIG. 5.

The carrier has a proximal end, a distal end, and a mounting surface 74 which is open in the lateral and distal directions. In a preferred embodiment, an ultrasonic imaging transducer 56 is mounted in a hole (not shown) through the mounting surface 74 of the housing. The mounting surface 74 is defined by two open major surfaces. The first major surface 59 is substantially planar. The second major surface 58 intersects the first major surface 59 at an angle of approximately 45°. Since the ultrasonic transducer 56 is mounted on to the first major surface 59, a gap may form 57 between the ultrasonic transducer 56 and the second major surface 58. The gap may be filled with an adhesive substance 54 so that the ultrasonic transducer 56 and the mounting surface 74 can have a relatively smooth contour. This configuration allows for the free flow of liquid over the transducer 56 so as to remove the possibility of bubbles congregating on the surface of the ultrasonic imaging transducer 56. Thus, removing the potential for smearing or obscuring the image shown the user on the monitoring screens.

Figure 5:
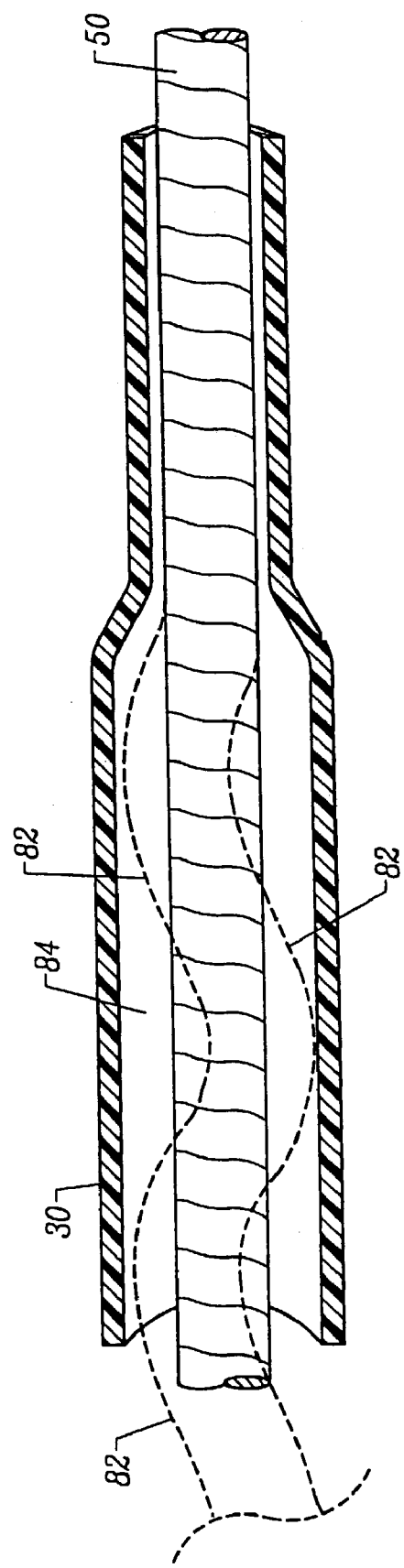
FIG. 5 illustrates a catheter body with an enlarged lumen providing sufficient annular clearance to localize drive cable failure.

Referring now to FIG. 5, the benefit of reducing the diameter of the drive cable 50 is illustrated. A reduced outer diameter of the drive cable 50 increases the annular clearance 84 between the drive cable 50 and the tubular walls of the catheter body 18. When a carrier 52, which in this case includes an ultrasonic transducer 56, is being advanced through a lumen 32 of the catheter body 18 at the distal end of a drive cable 50. It is possible that the carrier 52 will encounter a bent region or come in contact with the wall of the catheter body 18. Pressure between the carrier 52 and the wall will arise in a small localized area. As more force is applied to the drive cable 50, the pressure between the carrier 52 and the catheter body 18 may exceed the burst pressure of the wall of the catheter body 18. In that case, the wall will fail at the point of contact and the carrier may protrude out of the lumen 32 and into the blood vessel itself. This is potentially a very serious problem. At a minimum, the catheter system has failed and will have to be removed from the patient. Furthermore, the carrier 52 and the drive cable 50 are now exposed and may come into contact with the blood vessel wall and injure the patient. To avoid this type of failure, the carrier 52 which does encounter a kink or bend has the ability to buckle or distort due to the increased annular clearance 84. This failure will cause the drive cable 50 to buckle or distort in a sinusoidal fashion 82 within the proximal sheath 30. This buckling or distortion creates additional frictional forces which will quickly cause enough drag to cause the drive cable to fail in a safe manner as a result of the friction between the buckled drive cable and the enlarged lumen.

Although the foregoing invention has been described in detail for purposes of clarity of understanding, certain modifications will be obvious to those skilled in the art. Thus, the scope of the invention should be construed with reference to the appended claims including the full range of equivalents to which the inventor is entitled.

What is claimed is:

1. A catheter comprising:
a catheter body comprising (a) a proximal portion having a proximal end, a distal end and a lumen extending therebetween and (b) a distal portion having a proximal end, a distal end and a lumen extending therebetween;
connector means to releasably connect the distal and proximal portions end-to-end so as to join the lumens of the proximal and distal portions together in a continuous, axially fixed relationship; and
a drive cable axially translatable and rotatably disposed within the lumens when the proximal and distal portions are joined together, and an ultrasonic imaging transducer carried at the distal end o the drive cable.

2. The catheter of claim 1, further comprising a hub secured to the proximal end of the proximal portion of the catheter body and secured to a proximal end of the drive cable.

3. The catheter of claim 1, wherein the connector means comprises a pair of mating Luer connectors.

4. The catheter of claim 1, wherein the drive cable is rotatable.

5. The catheter of claim 1, wherein the catheter body is constructed of a material selected from a group consisting of a polymer, a plastic material or a polyetheretherketone (PEEK).

6. The catheter of claim 1, wherein the distal portion of the catheter body is exchangeable with another distal portion of the catheter body.

7. The catheter of claim 6, wherein the one distal portion of the catheter body comprises a relatively short guidewire access lumen and the other distal portion of the catheter body comprises a relatively long guidewire access lumen.

8. A catheter comprising:
a tubular catheter body comprising a proximal portion, a distal portion, and a lumen extending through said portions;
a drive cable rotatably received in the lumen;
connector means to releasably connect the distal and proximal portions end-to-end so as to join the lumens of the proximal and distal portions together in a continuous, axially fixed relationship, wherein the connector means comprise first and second connectors that are coupled to the proximal and distal portions, respectively.

9. The catheter of claim 8, wherein the proximal portion of the catheter body comprises a proximal tube section and a distal tube section which are joined together in a telescopic engagement.

10. The catheter of claim 8, further comprising an ultrasonic imaging transducer carried on a distal end of the drive cable.

11. A method for positioning a catheter within a selected region of a patient's vasculature using a catheter system comprising a catheter body having a proximal end, a distal end and a lumen extending therebetween and a plurality of distal portions each having a proximal end, a distal end, a primary lumen and a guidewire lumen; connector means to releasably connect to connect a selected one of the distal portions to the proximal portion end-to-end so as to join the lumen of the proximal portion to the primary lumen of the selected distal portion together in a continuous, axially fixed relationship; and a drive cable which can be disposed within the joined lumens when the proximal and selected distal portion are joined together, the method comprising the steps of:

advancing a guidewire into the patient's vasculature;
selecting one of the distal portions;
releasably connecting the selected distal portion to the proximal portion using the connector means;
introducing the guidewire lumen of the selected distal portion of the catheter body over the guidewire; and
advancing the catheter body over the guidewire.

12. A method as in claim 11, wherein a work element is secured on a distal end of the drive cable and the work element is disposed within the primary lumen, the method further comprising:
moving the drive cable to move the work element within the primary lumen of the distal portion of the catheter body.

13. The method of claim 12, wherein the work element is an ultrasonic imaging transducer carried at the distal end of the drive cable.

14. The method of claim 11, further comprising the step of exchanging a first of said plurality of distal portions of the catheter body, having a first guidewire lumen length, with a second of said plurality of distal portions of the catheter body, having a second guidewire lumen length.

15. A catheter comprising:
a tubular catheter body having a proximal portion, a distal portion, and a lumen extending therethrough;
a drive cable rotatably received in the lumen;
means for localizing drive cable failure to the proximal portion; and an ultrasonic imaging transducer carried on a distal end of the drive cable, and wherein the means for localizing comprises a proximal diameter of the lumen which is enlarged relative to a distal diameter so that there is sufficient annular clearance between the drive cable and an inner wall of the proximal portion so as to localize drive cable failure to the proximal portion.

16. A catheter as in claim 15, further comprising a hub on a proximal end of the catheter body, wherein the hub has a lumen which receives the drive cable and which is enlarged relative to the drive cable.

17. A catheter comprising:
a catheter body comprising (a) a proximal portion having a proximal end, a distal end and a lumen extending therebetween and (b) a distal portion having a proximal end, a distal end and a lumen extending therebetween;
connector means for releasably connecting the distal and proximal portions end-to-end so as to join the lumens of the proximal and distal portions together in a continuous, axially fixed relationship;
a drive cable disposed within the lumens when the proximal and distal portions are joined together; and
a proximal tube and a distal tube joined together in a telescopic engagement, the proximal tube and the distal tube being secured on the proximal portion.

18. A catheter comprising:

a catheter body comprising (a) a proximal portion having a proximal end, a distal end and a lumen extendingtherebetween and (b) a distal portion having a proximal end, a distal end and a lumen extending therebetween;

connector means to releasably connect the distal and proximal portions end-to-end so as to join the lumens of the proximal and distal portions together in a continuous, axially fixed relationship;

a drive cable axially translatable and rotatably disposed within the lumens when the proximal and distal portions are joined together; and a hub secured to the proximal end of the proximal portion of the catheter body and secured to a proximal end of the drive cable.

19. A catheter comprising:

a tubular catheter body comprising a proximal portion, a distal portion, and a lumen extending through said portions;

a drive cable rotatably received in the lumen;

connector means to releasably connect the distal and proximal portions end-to-end so as to join the lumens of the proximal and distal portions together in a continuous, axially fixed relationship, wherein the proximal portion of the catheter body comprises a proximal tube section and a distal tube section which are joined together in a telescopic engagement.

* * * * *